United States Patent [19]
Clouet

[11] Patent Number: 5,270,389
[45] Date of Patent: Dec. 14, 1993

[54] POLYURETHANES CONTAINING VINYL SEQUENCES, THEIR PRODUCTION PROCESS AND THEIR APPLICATION IN THE FORMULATION OF PAINTS

[75] Inventor: Gilbert Clouet, La Wantzenau, France

[73] Assignee: Cray Valley S.A., France

[21] Appl. No.: 838,820

[22] PCT Filed: Oct. 18, 1990

[86] PCT No.: PCT/FR90/00755
§ 371 Date: May 18, 1992
§ 102(e) Date: May 18, 1992

[87] PCT Pub. No.: WO91/05767
PCT Pub. Date: May 2, 1991

[30] Foreign Application Priority Data
Oct. 19, 1989 [FR] France .................. 89 13705

[51] Int. Cl.$^5$ ............................................. C08G 18/04
[52] U.S. Cl. ..................................... 525/123; 528/28;
528/65; 528/66; 528/73; 528/75; 528/76;
528/80; 528/83; 528/85
[58] Field of Search .................. 525/123; 528/28, 65,
528/66, 73, 75, 76, 80, 83, 85

[56] References Cited
U.S. PATENT DOCUMENTS
4,053,446 10/1977 Watabe et al. .................. 528/75

*Primary Examiner*—Maurice J. Welsh
*Attorney, Agent, or Firm*—Finnegan, Henderson, Farabow, Garrett & Dunner

[57] ABSTRACT

Said polyurethanes contain patterns of the type (Ia) or (Ib) with A=alkyl, cycloalkyl, aryl, arylalkyl or alkylaryl, or polyoxyalkylene or polyester; D=alkylene, cycloalkylene, arylene, alkylarylene or arylalkylene, and can contain at least one heteroatom; E=(i), in which case G represents the hydrocarbonated skeleton of an organic compound containing at least two alcohol functions, or (ii), in which case G represents the hydrocarbonated skeleton of an organic compound containing at least two isocyanate functions, and Pv=a polymer sequence from at least one vinyl monomer. The presence of vinyl sequences in said polyurethanes makes it possible, in particular, to improve the stability when exposed to sunlight (UV) of paints with a polyurethane base, thereby adding a sheen to said paints.

10 Claims, No Drawings

POLYURETHANES CONTAINING VINYL SEQUENCES, THEIR PRODUCTION PROCESS AND THEIR APPLICATION IN THE FORMULATION OF PAINTS

The present invention relates to the introduction of vinyl sequences into polyurethanes. It therefore relates to polyurethanes containing vinyl sequences, to production processes for these polyurethanes and to their application in the formulation of paints.

Thiuram disulphides are known as agents having the triple function of initiator, chain transfer agent and terminating agent (denoted by the abbreviation "iniferters") in the free radical polymerisation of vinyl monomers. Thus, tetraalkylthiuram disulphide iniferters have been described by Takayuki Ostu et al. in "Makromol. Chem. Rapid., Commun. 3, 127–132 (1982). Functional thiuram disulphides are proposed as iniferters in European Patent Application EP-A-0,237,792, the proposed functional groups comprising the hydroxyl, carboxyl and amine groups.

The present invention relates to the application of some functional thiuram disulphide iniferters in the production of vinyl polymers in which the end groups may, in their turn, be fused with an organic compound containing at least two alcohol groups or two isocyanate groups.

The present invention therefore firstly relates to a polyurethane containing units of the type $$\begin{array}{c}
\text{A} \\ \diagdown \\
\text{--G--E--D} \diagup \text{N--C--S--Pv--S--C--N} \diagdown \text{D--E--} \\
\phantom{--G--E--D\diagup}\underset{\text{S}}{\|}\phantom{--\text{Pv--S--}}\underset{\text{S}}{\|}
\end{array} \quad \text{(Ia)}$$

or $$\begin{array}{c}
\text{--G--E--D} \diagdown \phantom{\text{N--C--S--Pv--S--C--N}} \diagup \text{D--E--} \\
\phantom{--G--E--D}\diagdown \text{N--C--S--Pv--S--C--N}\diagup \\
\text{--G--E--D} \diagup \underset{\text{S}}{\|}\phantom{--\text{Pv--S--}}\underset{\text{S}}{\|} \diagdown \text{D--E--}
\end{array} \quad \text{(Ib)}$$

where:

A is chosen from alkyl, cycloalkyl, aryl, arylalkyl and alkylaryl groups and the polyoxyalkylene and polyester sequences, D is chosen from alkylene, cycloalkylene, arylene, alkylarylene and arylalkylene groups and may contain at least one hetero-atom, such as nitrogen or oxygen, E represents:
an $$-\text{NH}-\underset{\underset{\text{O}}{\|}}{\text{C}}-\text{O}-$$

group, in which case G represents the hydrocarbon backbone of an organic compound containing at least two alcohol groups, or
an $$-\text{O}-\underset{\underset{\text{O}}{\|}}{\text{C}}-\text{NH}$$

group, in which case G represents the hydrocarbon backbone of an organic compound containing at least two isocyanate groups, and Pv represents a polymer sequence resulting from at least one vinyl monomer.

These polyurethanes are preferably such that the polymer sequence Pv has a number-average molecular mass of between $10^2$ and $10^6$ approximately and more particularly between $10^3$ and $10^5$ approximately.

They mainly have a linear character in the case where G represents the hydrocarbon backbone of an organic compound not containing more than two alcohol or isocyanate groups, although secondary reactions of isocyanates on the urethane bonds may lead to allophanate bonds and thus to partial crosslinking. In the case where G represents the hydrocarbon backbone of an organic compound containing more than two alcohol or isocyanate groups, the polyurethanes according to the invention are crosslinked products.

The presence of vinyl sequences in these polyurethanes makes it possible, in particular, to improve the stability to sunlight (UV) of paints based on polyurethanes and to impart a gloss to these paints.

The alkyl and alkylene groups involved, respectively, in the definitions of A and D are especially $C_1$–$C_{12}$ and in particular $C_1$–$C_6$ groups; the cycloalkyl and cycloalkylene groups are especially monocyclic or polycyclic $C_3$–$C_{12}$ and in particular $C_5$–$C_7$ groups; the aryl and arylene groups are especially $C_6$–$C_{15}$ groups including one or more aromatic rings, such as phenyl or naphthyl.

The polyoxyalkylene sequence which may be involved in the definition of A may be represented by one of the following formulae:

$$R_{10}-O+CH_2-CH_2-O+_c CH_2-CH_2-$$

$$R_{10}-O+CH_2-\underset{\underset{\text{CH}_3}{|}}{\text{CH}}-O+_c CH_2-\underset{\underset{\text{CH}_3}{|}}{\text{CH}}-$$

$$R_{10}-O+\underset{\underset{\text{CH}_3}{|}}{\text{CH}}-CH_2-O+_c \underset{\underset{\text{CH}_3}{|}}{\text{CH}}-CH_2-$$

$$R_{10}-O+(CH_2)_4-O+_c (CH_2)_4-$$

where:

$R_{10}$ represents an alkyl, cycloalkyl or aryl radical; and
c ranges from 1 to 1,000, and preferably from 1 to 200.

The polyester sequence which may be involved in the definition of A may be represented by one of the following formulae:

$$R_{11}-\underset{\underset{\text{O}}{\|}}{\text{C}}-O-R_{12}+O-\underset{\underset{\text{O}}{\|}}{\text{C}}-R_{13}-\underset{\underset{\text{O}}{\|}}{\text{C}}-O-R_{12}\overline{)_d}$$

$$R_{11}+\underset{\underset{\text{O}}{\|}}{\text{C}}-R_{13}-\underset{\underset{\text{O}}{\|}}{\text{C}}-O-R_{12}\overline{)_d}; \text{ and}$$

$$R_{11}+O-\underset{\underset{\text{O}}{\|}}{\text{C}}-R_{13}-\underset{\underset{\text{O}}{\|}}{\text{C}}-R_{12}\overline{)_d}$$

where:

$R_{11}$ is as defined above for $R_{10}$;

$R_{12}$ and $R_{13}$ are chosen from alkylene, cycloalkylene, arylene, alkenylene and alkenylarylene groups and may contain at least one hetero-atom and/or at least one

radical, $R_{14}$ being chosen from alkyl, cycloalkyl and aryl groups and being able to contain substituents; and d ranges from 1 to 300, and preferably from 1 to 50.

The following may be mentioned in particular as vinyl monomers from which the polymer sequence Pv may have resulted:

an alkyl acrylate or methacrylate, the alkyl group of which is straight-chain or branched and contains, if appropriate, at least one hetero-atom in the form, for example, of a halogen atom or a carbonyl, hydroxyl or amino group, possesses from 1 to 20 carbon atoms, such as methyl, ethyl, n-butyl, tert-butyl, 2-ethylhexyl, stearyl, 2,2,2-trifluoroethyl, hydroxyethyl, hydroxyethylimidazolidone and hydroxyethyloxazolidone acrylates and methacrylates, an aryl acrylate or methacrylate, such as benzyl and phenyl methacrylate, a vinyl-aromatic hydrocarbon, such as styrene, vinyltoluene, α-methylstyrene, 4-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene, an epoxy acrylate or methacrylate, such as glycidyl acrylate and methacrylate, 2-epoxyethylbicyclo[[2.2.1]hept-5(6)-yl (meth)acrylate and the epoxidation product of dicyclopentenyloxyethyl acrylate, a dialkylaminoalkyl acrylamide or methacrylamide, acrylate or methacrylate and their quaternary salts, 2-(2-norbornyloxy)ethyl acrylate and methacrylate and 2-(2-dimethanodecahydronaphthyloxy)ethyl acrylate and methacrylate, an unsaturated nitrile, such as acrylonitrile or methacrylonitrile, an N-substituted maleimide, such as N-ethylmaleimide, N-isopropylmaleimide, N-n-butylmaleimide, N-isobutylmaleimide, N-tert-butylmaleimide, N-n-octylmaleimide, N-cyclohexylmaleimide, N-benzylmaleimide and N-phenylmaleimide, an anhydride of an unsaturated dicarboxylic acid, such as maleic anhydride, itaconic anhydride, citraconic anhydride or tetrahydrophthalic anhydride, acrylic acid or methacrylic acid, a polyol acrylate or methacrylate, such as the diacrylates and dimethacrylates of ethylene glycol, propylene glycol, 1,3-butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,2-diethyl-1,3-propanediol, diethylene glycol, dipropylene glycol, triethylene glycol, tripropylene glycol, tetraethylene glycol, tetrapropylene glycol, trimethylolethane, trimethylolpropane, glycerol and pentaerythritol, the, triacrylates and trimethacrylates of trimethylolethane, trimethylolpropane, glycerol and pentaerythritol, the tetraacrylates and tetramethacrylates of pentaerythritol, the di(meth)acrylates to hexa(meth)acrylates of dipentaerythritol and the poly(meth)acrylates of monoethoxylated or polyethoxylated or monopropoxylated or polypropoxylated polyols, such as triethoxylated trimethylolpropane triacrylate and trimethacrylate and tripropoxylated trimethylolpropane triacrylate and trimethacrylate; tripropoxylated glycerol triacrylate and trimethacrylate and tetraethoxylated pentaerythritol triacrylate, trimethacrylate, tetraacrylate and tetramethacrylate, a diene, such as 1,3-butadiene, isoprene, 1,3-pentadiene, 1,4-pentadiene, 1,4-hexadiene, 1,5-hexadiene, 1,9-decadiene, 5-methylene-2-norbornene, 5-vinyl-2-norbornene, 2-alkyl-2,5-norbornadienes, 5-ethylidene-2-norbornene, 5-(2-propenyl)-2-norbornene, 5-(5-hexenyl)-2-norbornene, 1,5-cyclooctadiene, bicyclo[2.2.2]octa-2,5-diene, cyclopentadiene, 4,7,8,9-tetrahydroindene and isopropylidenetetrahydroindene, a vinyl or vinylidene halide, such as vinyl bromide and vinyl and vinylidene chlorides, vinyl esters, such as vinyl acetate and vinyl crotonate; 9-vinylcarbazole, vinyl-2-pyridine, vinyl-4-pyridine, 1-vinyl-2-pyrrolidinone, vinyltrimethoxysilane, vinyltrimethylsilane and 1-vinylimidazole, and trialkylsilyl or trialkoxysilyl methacrylates, such as 3-(trimethoxysilyl)propyl methacrylate, trimethylsilyl methacrylate and 2-(trimethylsilyloxy)ethyl methacrylate.

The polyurethanes according to the invention in which E represents an

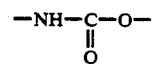

group and G represents the hydrocarbon backbone of an organic compound containing at least two alcohol groups may be prepared by reacting a polymer of formula:

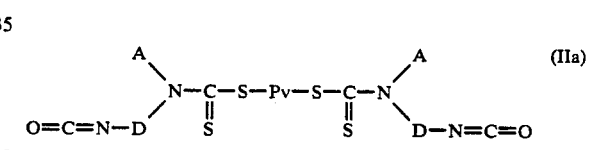

or

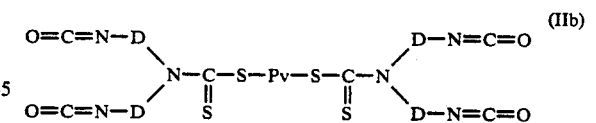

if appropriate as a mixture with at least one other organic compound containing at least two isocyanate groups, with at least one compound of formula:

if appropriate as a mixture with at least one other organic compound containing at least two alcohol groups.

The following may be mentioned as examples of compounds of formula (III): ethylene glycol, propanediol, butane-1,4-diol, butane-2,3-diol, 2,2-dimethylpropane-1,3-diol, ethylene glycol adipate, polyethylene glycols, polypropylene glycols and random and block ethylene oxide/propylene oxide copolymers having a molecular mass of between about 400 and 40,000, polyhydroxy compounds having a molecular mass of between about 400 and about 600, polyethers and polyesters.

The reaction of the polymer of formula (IIa) or (IIb) and the compound of formula (III) is preferably carried out in the presence of a catalyst, such as iron acetylacetonate, a tertiary amine, a lead naphthenate or cobalt naphthenate or a tin salt, such as dialkyltin dicarboxylates, and preferably using an [NCO]/[OH] molar ratio of the isocyanate groups in the polymer (IIa) or (IIb) to the alcohol groups in the compound (III) essentially equal to 1.

The following procedure may be used in order to prepare the polymer of formula (IIa):
in a first step, a compound of formula:

   (IV)

is reacted with a haloacid XH in order to obtain the compound of formula:

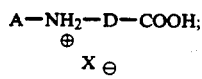   (V)

in a second step, the compound (V) is reacted with a halogenating agent in order to obtain the compound of formula:

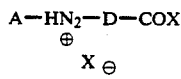   (VI)

in a third step, the compound (VI) is reacted with a nitride of formula:

   (VII)

where R is an alkyl, cycloalkyl or aryl radical or a combination of at least two of these radicals, in order to obtain the compound of formula:

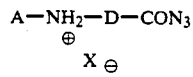   (VIII)

in a fourth step, the compound (VIII) is reacted with carbon disulphide in the presence of at least one oxidising agent in order to obtain the compound of formula:

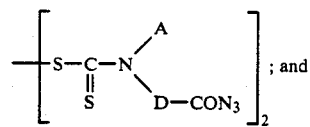   (IX)

in a fifth step, the free radical polymerisation of a vinyl monomer Mv is carried out in the presence of the compound (IX) as an agent having the triple function of initiator, chain transfer agent and terminating agent.

The general reaction conditions for the first step are in particular as follows:

The reaction is carried out at a temperature generally between about 0° C. and ambient temperature. In a particular embodiment, a haloacid, such as, for example, HCl is added slowly to the amino acid (IV) mole by mole in order to give the salt (V).

The reaction conditions for the second step are in particular as follows:

The reaction is carried out at a temperature generally between about 20° and 120° C. and preferably at about 80°-110° C. For example, the reaction is carried out in a pyridine medium. The halogenating agent may be, inter alia, thionyl chloride.

The reaction conditions for the third step are in particular as follows:

The reaction is generally carried out at about 60° C. The reaction is preferably carried out in a polar solvent medium, such as dimethylformamide (DMF) and tetrahydrofuran (THF).

According to a particular embodiment the compound (VI) is mixed with trimethylsilane nitride (Me$_3$Si—N$_3$) as compound (VII) in one of the solvents indicated above and is refluxed for about 13 hours. The compound (VIII) is a solid recovered by filtering off.

The reaction conditions for the fourth step are in particular as follows:

The reaction is generally carried out at about ambient temperature. The reaction is generally carried out using an essentially equimolar ratio of CS$_2$ to the quaternised amine (VIII) or non-quaternised amine.

The oxidising agent is added, for example, in an amount of about 1 mole per mole of CS$_2$ and is chosen, for example, from iodine, hydrogen peroxide, alkali metal hypochlorites, alkyl hydroperoxides and aryl hydroperoxides and potassium hexacyanoferrate.

The reaction may be carried out in the presence of a tertiary amine (for example triethylamine or pyridine), in an amount of at least 2 moles per mole of quaternised amine and 1 mole per mole of non-quaternised amine. The reaction may be carried out in a solvent medium, it being possible for CS$_2$ or the tertiary amine to serve as solvent.

The reaction of the fifth step may be carried out under a pressure ranging up to about 30 bars and, if appropriate, in the presence of a common solvent for the monomer Mv and the polymer sequence Pv, such as an aromatic hydrocarbon (toluene, xylene, etc.) or an ether (tetrahydrofuran or diglyme).

The polymerisation conditions for the fifth step are, of course, variable depending on the nature of the vinyl monomer Mv, the solvent and the pressure, but generally comprise a temperature of between 50° C. and 130° C. approximately and a time of between 0.5 and 48 hours approximately. When a low temperature and/or a short time are chosen, the intermediate formation of a polymer of formula:

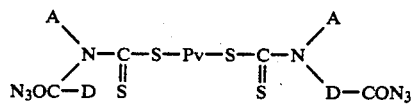   (X)

may take place, which polymer is then converted to a polymer of formula (IIa) by refluxing in solution in a solvent appropriate to the polymer chain, for example toluene, for about 12 to 24 hours.

According to one variant, the compound (IV) or (V) is reacted, in the presence of a tertiary amine, such as triethylamine, and an alkyl chloroformate or cycloalkyl chloroformate such as ClCO$_2$C$_2$H$_5$, with an alkali metal nitride in order to obtain, respectively, a compound of formula:

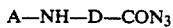   (XI)

or the compound of formula (VIII), which is then subjected to the fourth step as defined above.

According to another variant, it is possible, in the fifth step, to heat the compound (IX) in a solvent medium in order to obtain the compound of formula:

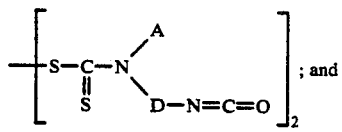 (XII)

in a sixth step, to carry out the free radical polymerisation of a vinyl monomer Mv in the presence of the compound of formula (XII) as agent having the triple function of initiator, chain transfer agent and terminating agent.

The amount of iniferter (IX) or (XII) introduced in the fifth or sixth step is generally between $5 \times 10^{-5}$ mol/l and 0.1 mol/l with respect to the vinyl monomer.

In order to prepare the polymer of formula (IIa), it is also possible to use a process consisting in reacting a polymer of formula:

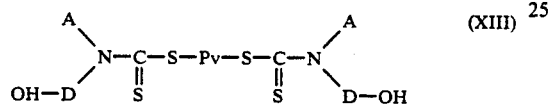 (XIII)

with an organic compound containing at least two isocyanate groups, one of which is much more reactive than the other with respect to the hydroxyl groups, the molar ratio of the said organic compound to the polymer (XIII) being at least 2. An example of such an organic compound which may be mentioned in particular is isophorone diisocyanate.

In order to prepare the compound of formula (XII) it is also possible to react a compound of formula:

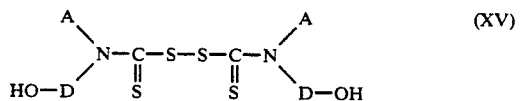 (XV)

with an organic compound containing at east two isocyanate groups, one of which is much more reactive than the other with respect to the hydroxyl groups, the molar ratio of the said organic compound to the compound (XV) being at least 2.

The following procedure may be used in order to prepare the polymer of formula (IIb):
in a first step, a compound of formula:

HOOC—D—NH—D—COOH (XVI)

is reacted with a haloacid XH in order to obtain the compound of formula:

HOOC—D—NH$_2$—D—COOH (XVII)
⊕
X ⊖ in a second step, the compound (XVII) is reacted with a halogenating agent in order to obtain the compound of formula:

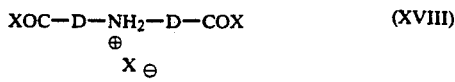
XOC—D—NH$_2$—D—COX (XVIII)
⊕
X ⊖ in a third step, the compound (XVIII) is reacted with a nitride of formula (VII) in order to obtain the compound of formula:

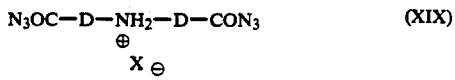
N$_3$OC—D—NH$_2$—D—CON$_3$ (XIX)
⊕
X ⊖ in a fourth step the compound (XIX) is reacted with carbon disulphide, in the presence of at least one oxidising agent, in order to obtain the compound of formula:

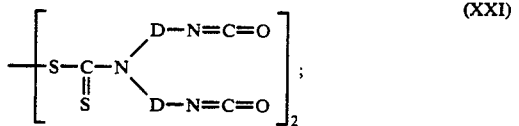 (XX)

in a fifth step the free radical polymerisation of a vinyl monomer Mv is carried out in the presence of the compound (XX) as an agent having the triple function of initiator, chain transfer agent and terminating agent.

The general reaction conditions are analogous to those already described for the synthesis of a polymer of formula (IIa) from a compound of formula (IV). The same process variants may be envisaged, in particular that consisting in heating the compound (XX) in a solvent medium in order to obtain the compound of formula:

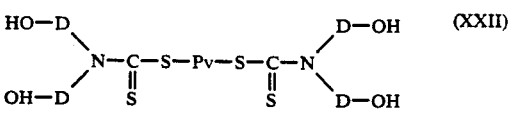 (XXI)

and then, in a sixth step, in carrying out the polymerisation of Mv in the presence of the compound (XXI) acting as iniferter.

In order to prepare the polymer of formula (IIb) it is also possible to use a process consisting in reacting a polymer of formula:

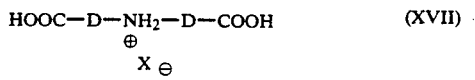 (XXII)

with an organic compound containing at least two isocyanate groups, one of which is much more reactive than the other with respect to the hydroxyl groups, the molar ratio of the said organic compound to the polymer (XXII) being at least 2. An example of such an organic compound which may be mentioned in particular is isophorone diisocyanate.

In order to prepare the compound of formula (XXI), it is also possible to react a compound of formula:

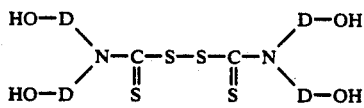 (XXIII)

with an organic compound containing at least two isocyanate groups, one of which is much more reactive than the other with respect to the hydroxyl groups, the molar ratio of the said organic compound to the compound (XXIII) being at least 2.

It is expedient to note the following restriction for implementing the process variant comprising a sixth step for polymerisation of Mv in the presence of a compound of formula (XII) or (XXI): in this case the monomer Mv may not carry an alcohol, acid or anhydride functional group; in other words it cannot be chosen from acrylic and methacrylic acids, hydroxylated (meth)acrylates or polyol (meth)acrylates and unsaturated dicarboxylic acid anhydrides.

The complete developed formula of a polyurethane according to the invention in which E represents an

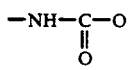

group and G represents the hydrocarbon backbone of an organic compound containing at least two alcohol groups is written as follows, K denoting the unit of type (Ia) or (Ib) and it being assumed that the [NCO]/[OH] ratio of the isocyanate groups in the polymer of formula (IIa) or (IIb) to the alcohol groups in the compound (III) is 1:

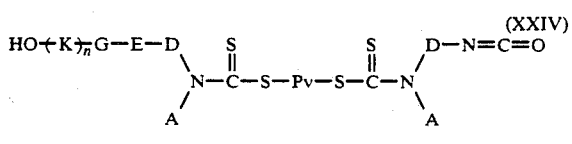 (XXIV)

or

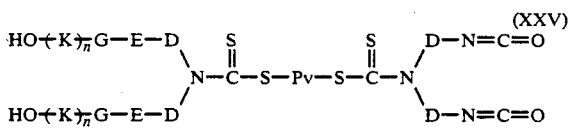 (XXV)

n being an integer between 1 and 50 approximately inclusive.

The polyurethanes according to the invention in which E represents an

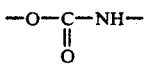

group and G represents the hydrocarbon backbone of an organic compound containing at least two isocyanate groups may be prepared by reacting a polymer of formula:

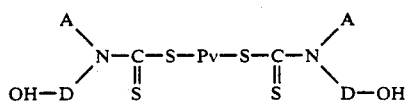 (XIII)

if appropriate as a mixture with at least one other organic compound containing at least two alcohol groups, with at least one compound of formula:

$$O=C=N-G-N=C=O \quad (XIV)$$

if appropriate as a mixture with at least one other organic compound containing at least two isocyanate groups. Polymers (XIII) are already known from the abovementioned document EP-A-237,792.

Compounds of formula (XIV) which may be mentioned are, inter alia, hexamethylene diisocyanate, trimethylhexamethylene diisocyanate, 1-methyl-2,4-diisocyanatocyclohexane, dicyclohexylmethane 4,4'-diisocyanate, toluylene diisocyanate, 4,4'-diphenylmethane diisocyanate, isophorone diisocyanate and xylylene diisocyanate.

The reaction of the polymer of formula (XIII) or (XXII) and the compound of formula (XIV) is preferably carried out in the presence of an anhydrous solvent such as toluene at a temperature of between about 20° C. and the boiling point of the solvent. It is preferably carried out in the presence of a catalyst of the same type as that described for the reaction between a polymer (IIa) or (IIb) and the compound (III), and preferably using an [NCO]/[OH] molar ratio of the isocyanate groups in the compound (XIV) to the alcohol groups in the polymer (XIII) or (XXII) essentially equal to 1.

The complete developed formula of a polyurethane according to the invention in which E represents an

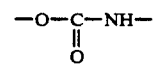

group and G represents the hydrocarbon skeleton of an organic compound containing at least two isocyanate groups is written as follows, K denoting the unit of type (Ia) or (Ib) and it being assumed that the [NCO]/[OH] ratio of the isocyanate groups in the compound (XIV) to the alcohol groups in the polymer of formula (XIII) or (XXII) is 1:

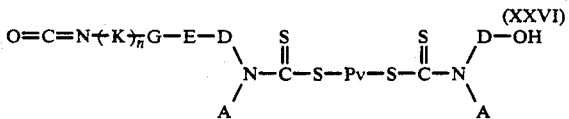 (XXVI)

or

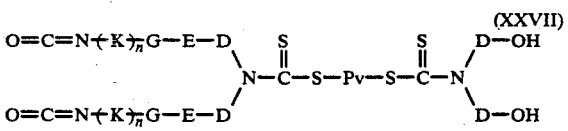 (XXVII)

n being an integer between 1 and 50 approximately inclusive.

EXAMPLE 1

Preparation of hydrochlorinated 4-(methylamino)-butyric acid chloride

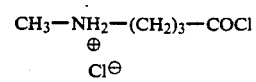

The starting hydrochlorinated 4-(methylamino)-butyric acid,

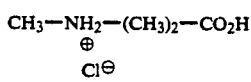

is available commercially. However, it is possible to quaternise the amine in bulk or in solution in ether by slow addition of an aqueous HCl solution at ambient temperature in an equimolar amount. The salt is extracted from the aqueous phase using $HCCl_3$.

76.8 g (0.5 mol) of hydrochlorinated 4-(methylamino)butyric acid are mixed with 146 ml (238 g; 2 mol) of thionyl chloride and 40.5 ml (39.5 g; 0.5 mol) of pyridine. The reaction mixture is refluxed until all of the solid has dissolved (over a period of about 1–4 hours). The excess $SOCl_2$ separated off by filtration. The solid is washed with chloroform and dried under vacuum.

EXAMPLE 2

Preparation of hydrochlorinated 3-azocarbonylpropyl(N-methyl)amine 17.2 g (0.1 mol) of hydrochlorinated 4-(methylamino)butyric acid chloride are dissolved in 350 ml of THF with 12.5 g (0.11 mol) of trimethylsilane nitride ($Me_3SiN_3$). The whole is refluxed for 13 hours. The precipitate is recovered by filtering off. It is then dissolved in methylene chloride, filtered off and dried over $Na_2SO_4$. After filtering, the methylene chloride is removed.

EXAMPLE 3

Alternative method for the preparation of 3-azocarbonylpropyl(N-methyl)amine

A suspension of 15.4 g (0.1 mol) of hydrochlorinated (4-methylamino)butyric acid suspended in acetone (400 ml) is cooled to 0° C. 30.3 g (0.3 mol) of triethylamine dissolved in 100 ml of acetone are added slowly. The mixture is stirred for a further 1 hour at 0° C. before adding 21.7 g (0.2 mol) of ethyl chloroformate dissolved in 100 ml of acetone. The reaction mixture is stirred for 1 hour at 0° C. before the dropwise addition of 26 g (0.4 mol) of sodium nitride in 400 ml of distilled water. After the end of the addition, stirring is continued for 4 hours at 0° C. The mixture is then poured into 2 liters of a water/ice mixture. The solid is recovered by filtering off. After dissolving in methylene chloride, it is dried over sodium sulphate. After filtering, the evaporation of $CH_2Cl_2$ is carried out under reduced pressure. 3-Azocarbonylpropyl(N-methyl)amine is obtained in a yield of 85%.

EXAMPLE 4

Preparation of the iniferter

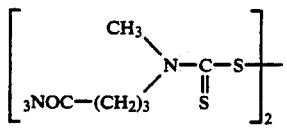

(a) 3 ml (0.05 mol) of CS, are added to 5.15 g (0.05 mol) of 3-azocarbonylpropyl(N-methyl)amine, obtained in Example 3, dissolved in 150 ml of chloroform, at ambient temperature, with stirring. 6.5 ml (5.05 g; 0.05 mol) of triethylamine are then introduced. 6.3 g (0.05 mol) of iodine in 50 ml of $HCCl_3$ are added to the reaction mixture. The reaction is allowed to proceed until all the iodine has been consumed (about 1 hour). The product is isolated by removing the ammonium iodide by washing with an ice/water mixture, then drying the solution and evaporating off the $HCCl_3$ under vacuum.

10 g (98%) of a product containing: 33.1% C; 4.1% H; 7.4% O, 29.5% S and 25.8% N are obtained.

(b) Using the hydrochlorinated azocarbonylpropyl(N-methyl)amine obtained in Example 2 as starting substance, the procedure of paragraph (a) above is followed except that, in this case, the triethylamine is added to the reaction mixture in an amount of 2 mol per 1 mol of starting hydrochlorinated compound.

EXAMPLES 5 TO 11

Free radical polymerisation of methyl methacrylate (Examples 5 to 8) or of n-butyl methacrylate (Examples to 9 to 11) in the presence of the iniferter of Example 4

General method

The polymerisations are carried out in round-bottomed flasks provided with a stirrer, which are sealed under vacuum or kept under an inert gas ($N_2$ or argon) after introducing the reagents. If the iniferter is soluble in the monomer the polymerisation is carried out as bulk polymerisation; in the contrary case, the monomer is diluted half-and-half with ethyl acetate or butyl acetate as solvent. The desired amount of iniferter, the monomer and, where appropriate, the solvent are introduced into the round-bottomed flask, which is then degassed. The polymerisation is carried out in the absence of light, by immersing the vessel in an oil bath thermostat-controlled at the required temperature, for the desired time. After polymerisation, the round-bottomed flask is withdrawn from the oil bath and cooled in an isopropanol/solid carbon dioxide mixture and the polymer is diluted with ethyl acetate and then precipitated dropwise in heptane. The precipitate or the resinous product obtained is collected in a sintered glass crucible, washed with heptane and dried at 45° C. for 12 hours under vacuum. The results are indicated in Table I below.

TABLE 1

| Ex. | Monomer | $[In] \times 10^3$ * | Temperature °C. | Polymerisation time (h) | $\overline{M}_n$ ** | I *** | Func. tionality **** |
|---|---|---|---|---|---|---|---|
| 5 |  | 61 | 60 | 72 | 41,000 | 2.5 | — |
| 6 |  | 92 | 70 | 48 | 29,000 | 1.9 | — |
| 7 | MMA | 70 | 85 | 24 | 25,000 | 1.7 | 2.1 |
| 8 |  | 95 | 95 | 24 | 8,000 | 1.4 | 1.9 |
| 9 |  | 60 | 95 | 24 | 10,000 | 1.5 | 2 |
| 10 | BMA | 85 | " | " | 9,000 | 1.4 | 2 |

TABLE 1-continued

| Ex. | Monomer | [In] × 10³ * | Temperature °C. | Polymerisation time (h) | $\overline{M}_n$ ** | I *** | Func. tionality **** |
|---|---|---|---|---|---|---|---|
| 11 | | 100 | " | " | 6,000 | 1.3 | 2 |

*[In] iniferter concentration in mol/l of monomer
**Mn: number-average molecular mass determined by GPC
***I: polydispersity index ($M_w/M_n$)
****determined by means of a Fourier transform infrared spectrometer from the NCO band at 2320 cm⁻¹.

EXAMPLE 12

Synthesis of the iniferter
N,N'-diethyl-N,N-bis(2-hydroxyethyl)thiuram disulphide

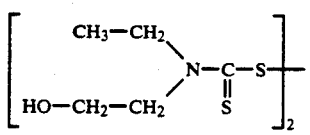

26.9 g (0.33 mol) of 2-ethoxyaminoethanol in 350 ml of HCCl₃ are brought into contact with 20 ml (0.33 mol) of CS₂ and 33 g (0.33 mol) of triethylamine. 42.8 g (0.33 mol) of iodine dissolved in 125 ml of chloroform are then added to the solution while keeping the temperature at 0° C. Stirring of the reaction mixture is continued until all the iodine has disappeared.

The mixture is washed with water and dried and the chloroform is then evaporated under a partial vacuum. A yellow viscous liquid is obtained (50 g, yield 90%).

EXAMPLES 13 TO 15

Polymerisation of methyl methacrylate in the presence of the iniferter of Example 12

The method is identical to that of Examples 5 to 11.
The results are given in Table II, $M_n$ and I having the same definition as in Table I.

TABLE II

| Ex. | [DHTD] | Polymerisation time (h) | Temperature °C. | $M_n$ | I | % of sulphur (by weight) |
|---|---|---|---|---|---|---|
| 13 | 30 | 48 | 85 | 30,000 | 1.9 | 0.42 |
| 14 | 60 | 24 | 95 | 17,000 | 1.7 | 0.75 |
| 15 | 90 | 24 | 95 | 7,000 | 1.4 | 1.82 |

[DHTD]: concentration of N,N'-diethyl-N,N'-bis(2-hydroxyethyl)-thiuram disulphide in mol/l of monomer

EXAMPLE 16

Preparation of polyurethane from poly(butyl methacrylate) α, ω- diisocyanate 30 g (9.1×10⁻² mol) of the compound of Example 11 and 30.3 g (6.33×10⁻² mol) of:

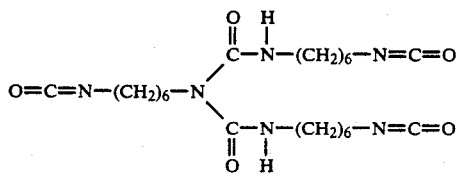

marketed by BAYER under the name "Desmodur N", and 105 g (0.105 mol) of an α,ω- dihydroxy-polyoxyethyelene having a mass of 1,000 are vigorously mixed. The temperature is then brought to 100° C. for 2 hours.

The film obtained is insoluble in N,N-dimethylacetamide. Its infrared spectrum, between the absorptions between 3270 and 3325 cm⁻¹ due to the vibrations of the N—H bonds and those between 1650 and 1740 cm⁻¹ due to the vibrations of the C═O bonds, reveals the presence of urethane bonds. The band corresponding to the isocyanate groups between 2300 and 2320 cm⁻¹ have completely disappeared.

EXAMPLE 17

Preparation of polyurethane from α, ω-dihydroxypoly(methyl methacrylate)

35 g (5×10⁻³ mol) of the polymer of Example 15 and 1.6 g (3.3×10⁻³ mol) of Desmodur N are vigorously mixed. The temperature of the reaction mixture is brought to 80° C. for 40 minutes. The infrared spectrum of the polyurethane obtained is qualitatively similar to that of Example 16 in respect of the absorptions due to the vibrations of the —N—H and —C═O bonds.

EXAMPLE 18

Preparation of the iniferter of formula

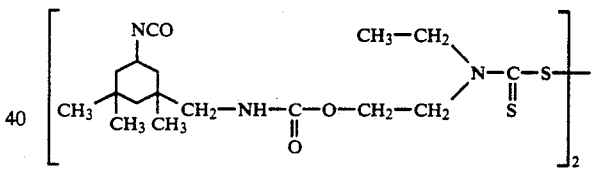

30 g (9.1×10⁻² mol) of the compound of Example 11 are added slowly, with stirring, so as to keep the reaction mixture at about 40° C., to 20.5 g (9.2×10⁻² mol) of isophorone diisocyanate dissolved in anhydrous toluene, into which 20 mg (3×10⁻⁵ mol) of dibutyltin dilaurate have been introduced. After the end of the addition, stirring of the mixture is continued at this temperature for a further 2 hours.

After evaporation of the solution, the determination of the isocyanate groups is carried out in accordance with the conventional n-dibutylamine technique.

The infrared spectrum has the band characteristic of isocyanate groups at 2310 cm⁻¹.

50 g (99%) of the compound are obtained, containing: 47.95% C; 6.95% H; 10.15% N; 23.16% S; 11.73% O.

EXAMPLE 19

Preparation of the polymer of formula:

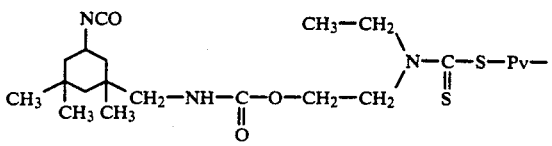

-continued

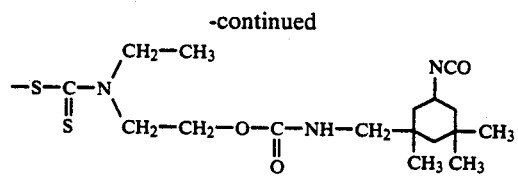

35 g ($5 \times 10^{-3}$ mol) of the polymer of Example 15 dissolved in anhydrous toluene are added slowly to a mixture of 2.22 g ($10^{-2}$ mol) of isophorone diisocyanate, anhydrous toluene and 10 mg ($1.5 \times 10^{-5}$ mol) of dibutyltin dilaurate, with stirring at 40° C. in the absence of atmospheric humidity. After the end of the addition, stirring of the mixture is continued for 2 hours at 40° C. A poly(methyl methacrylate) (PMMA) having the above formula, where Pv=PMMA, is recovered by precipitation in anhydrous hexane.

The determination of the isocyanate groups carried out by the conventional technique using n-dibutylamine gives an —NCO functionality of close to 2.

I claim:

1. Polyurethane containing units of the type

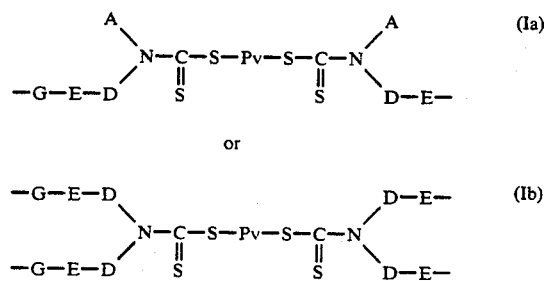

where:

A is chosen from alkyl, cycloalkyl, aryl, arylalkyl and alkylaryl groups and the polyoxyalkylene and polyester sequences, D is chosen from alkylene, cycloalkylene, arylene, alkylarylene and arylalkylene groups and may contain at least one hetero-atom, E represents:

an

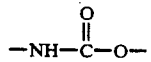

group bonded in the manner

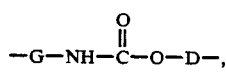

in which case G represents the hydrocarbon backbone of an organic compound containing at least two alcohol groups, an

group bonded in the manner

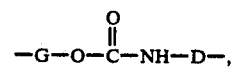

in which case G represents the hydrocarbon backbone of an organic compound containing at least two isocyanate groups, and Pv represents a polymer sequence resulting from at least one vinyl monomer.

2. Polyurethane according to claim 1, characterised in that the polymer sequence Pv has a number-average molecular mass of between $10^2$ and $10^6$.

3. Polyurethane according to claim 1, characterised in that the vinyl monomer is chosen from alkyl acrylates and methacrylates, the alkyl group of which contains, optionally, at least one hetero-atom, and aryl acrylates and methacrylates, vinyl-aromatic hydrocarbons, epoxy acrylates and methacrylates, dialkylaminoalkyl acrylamides and methacrylamides, acrylates and methacrylates and their quaternary salts, unsaturated nitriles, N-substituted maleimides, unsaturated dicarboxylic acid anhydrides, acrylic and methacrylic acids, polyol acrylates and methacrylates, dienes, vinyl halides and vinylidene halides, vinyl esters, trialkylsilyl methacrylates and trialkoxysilyl methacrylates, 9-vinylcarbazole, vinyl-2-pyridine, vinyl-4-pyridine, 1-vinyl-2-pyrrolidinone, vinyltrimethoxysilane, vinyltrimethylsilane and 1-vinylimidazole.

4. Process for the production of a polyurethane as defined in claim 1, E representing

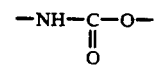

and G represents the hydrocarbon backbone of an organic compound containing at least two alcohol groups, characterised in that the polymer of formula:

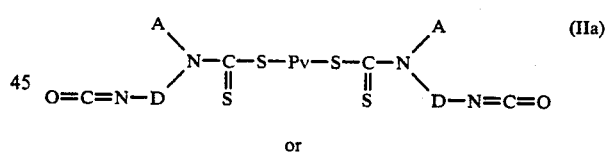

or

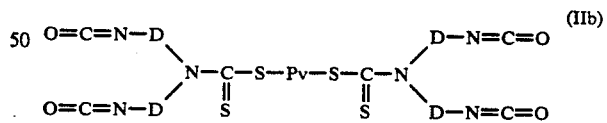

optionally as a mixture with at least one other organic compound containing at least two isocyanate groups, is reacted with at least one compound of formula:

optionally as a mixture with at least one other organic compound containing at least two alcohol groups.

5. Process according to claim 4, characterised in that in order to prepare the polymer of formula (IIa) or (IIb) an organic compound containing at least two isocyanate groups, one of which is much more reactive than the other with respect to hydroxyl groups, is reacted with: either a polymer of formula

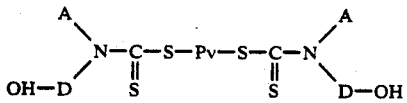 (XIII)

in order to obtain a polymer of formula (IIa), or a polymer of formula

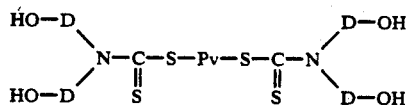 (XXII)

in order to obtain a polymer of formula (IIb), the molar ratio of the said organic compound to the polymer (XIII) or (XXII) being at least 2.

6. Process according to claim 5, characterised in that the organic compound containing at least two isocyanate groups, one of which is much more reactive than the other, is isophorone diisocyanate.

7. Process for the production of a polyurethane as defined in claim 1, E representing a

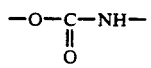

group and G representing the hydrocarbon backbone of an organic compound containing at least two isocyanate groups, by reacting a polymer of formula:

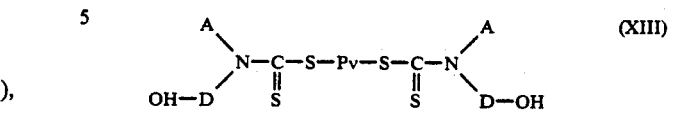 (XIII)

or

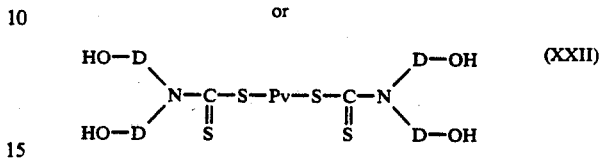 (XXII)

optionally as a mixture with at least one other organic compound containing at least two alcohol groups, with at least one compound of formula:

 (XIV)

optionally as a mixture with at least one other organic compound containing at least two isocyanate groups.

8. Process according to one of claims 4 or 7, characterised in that the reaction is carried out using an [NCO]/[OH] molar ratio essentially equal to 1.

9. Process according to one of claims 4, 7 or 8, characterised in that the reaction is carried out in the presence of a catalyst.

10. Paint formulation containing at least one polyurethane according to claim 1.

* * * * *